(12) United States Patent
Bojarski et al.

(10) Patent No.: US 6,599,289 B1
(45) Date of Patent: Jul. 29, 2003

(54) GRAFT ANCHOR

(75) Inventors: Ray Bojarski, Attleboro, MA (US);
Ben K. Graf, Madison, WI (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 09/523,067

(22) Filed: Mar. 10, 2000

(51) Int. Cl.[7] .............................. A61F 5/00; A61F 2/08
(52) U.S. Cl. .................... 606/60; 606/73; 623/13.14
(58) Field of Search .......................... 606/60, 72, 73, 606/104, 65, 232; 623/13.13, 13.14

(56) References Cited

U.S. PATENT DOCUMENTS

| | | | |
|---|---|---|---|
| 4,246,660 A | 1/1981 | Wevers | 3/1 |
| 4,275,717 A | 6/1981 | Bolesky | 128/92 |
| 4,462,395 A | 7/1984 | Johnson | 128/92 |
| 4,590,928 A | 5/1986 | Hunt et al. | |
| 4,602,635 A | 7/1986 | Mulhollan et al. | 128/334 |
| 4,605,414 A | 8/1986 | Czajka | 623/13 |
| 4,669,473 A | 6/1987 | Richards et al. | 128/334 |
| 4,708,132 A | 11/1987 | Silvestrini | 128/92 |
| 4,712,542 A | 12/1987 | Daniel et al. | 128/92 |
| 4,738,255 A | 4/1988 | Goble et al. | 128/92 |
| 4,741,330 A | 5/1988 | Hayhurst | 128/92 |
| 4,744,793 A | 5/1988 | Parr et al. | 623/13 |
| 4,750,492 A | 6/1988 | Jacobs | 128/335 |
| 4,772,286 A | 9/1988 | Goble et al. | 623/13 |
| 4,793,335 A | 12/1988 | Frey et al. | 128/92 R |
| 4,834,752 A | 5/1989 | Van Kampen | 623/13 |
| 4,870,957 A | 10/1989 | Goble et al. | 128/92 |
| 4,927,421 A | 5/1990 | Goble et al. | 606/73 |
| 4,946,468 A | 8/1990 | Li | 606/232 |

(List continued on next page.)

FOREIGN PATENT DOCUMENTS

| | | |
|---|---|---|
| DE | 1964950 A1 | 6/1998 |
| EP | 0279129 | 3/1991 |
| FR | 2590792 | 6/1987 |
| GB | 2248778 A | 4/1992 |
| GB | 2288739 A | 11/1995 |
| WO | WO 96/41574 | 12/1996 |
| WO | WO 98/11839 | 3/1998 |
| WO | WO 98/22048 | 5/1998 |

OTHER PUBLICATIONS

Howell, "Why the Double–Looped Semitendinosus and Gracilis Graft is Effective at Restoring Stability and Function to the ACL Reconstructed Knee", pp. 1–9.

"Techniques for ACL Reconstruction with Multi–Trac™ Drill Guide" ©Acufex Microsurgical, Inc. 1994, Mansfield, MA.

"Washerloc Tibial Fixation Device for Soft Tissue Grafts," Athrotek—an Intregral Park of Biomers Worldwide Team, ©1997 Arthrotek, Inc., Warsaw, IN.

GeoFit™ Screw & Washer System ©1997 Innovasive Devices, Inc., Marlborough, MA.

"Endo Pearl Bioabsorbable Implant" © 1999 Linvatec Corporation.

PCT International Search Report for International Application No. PCT/US 01/06845.

*Primary Examiner*—Cary E. O'Connor
(74) *Attorney, Agent, or Firm*—Fish & Richardson P.C.

(57) ABSTRACT

A device for securing a graft in a bone tunnel includes an anchoring member having a graft supporting surface. The anchoring member is configured to be positioned within the bone tunnel distal of an interference member with the graft retained by the graft supporting surface and extending proximally from the anchoring member. The anchoring member has an engaging surface for engaging a distal end of the interference member to limit movement of the graft relative to the interference member.

31 Claims, 7 Drawing Sheets

U.S. PATENT DOCUMENTS

| | | | |
|---|---|---|---|
| 4,950,271 A | 8/1990 | Lewis et al. | 606/102 |
| 4,960,420 A | 10/1990 | Goble et al. | 606/72 |
| 4,968,315 A | 11/1990 | Gatturna | 606/72 |
| 4,988,351 A | 1/1991 | Paulos et al. | 606/72 |
| 4,997,433 A | 3/1991 | Goble et al. | 606/64 |
| 5,013,316 A | 5/1991 | Goble et al. | 606/72 |
| 5,037,422 A | 8/1991 | Hayhurst et al. | 606/72 |
| 5,037,426 A | 8/1991 | Goble et al. | 606/96 |
| 5,041,129 A | 8/1991 | Hayhurst et al. | 606/232 |
| 5,108,431 A | 4/1992 | Mansat et al. | 623/13 |
| 5,129,902 A | 7/1992 | Goble et al. | 606/65 |
| 5,129,906 A | 7/1992 | Ross et al. | 606/77 |
| 5,139,520 A | 8/1992 | Rosenberg | 623/13 |
| 5,141,520 A | 8/1992 | Goble et al. | 606/232 |
| 5,147,362 A | 9/1992 | Goble | 606/72 |
| 5,152,790 A | 10/1992 | Rosenberg et al. | 623/13 |
| 5,176,682 A | 1/1993 | Chow | 606/72 |
| 5,176,691 A | 1/1993 | Pierce | 606/148 |
| 5,181,919 A | 1/1993 | Bergman et al. | 606/144 |
| 5,192,303 A | 3/1993 | Gatturna et al. | 606/232 |
| 5,209,756 A | 5/1993 | Seedhom et al. | 606/151 |
| 5,211,647 A | 5/1993 | Schmieding | 606/104 |
| 5,224,946 A | 7/1993 | Hayhurst et al. | 606/72 |
| 5,234,430 A | 8/1993 | Huebner | 606/60 |
| 5,266,075 A | 11/1993 | Clark et al. | 623/15 |
| 5,268,001 A | 12/1993 | Nicholson et al. | 606/72 |
| 5,306,290 A | 4/1994 | Martins et al. | 606/232 |
| 5,312,438 A | 5/1994 | Johnson | 606/232 |
| 5,314,427 A | 5/1994 | Goble et al. | 606/72 |
| 5,324,308 A | 6/1994 | Pierce | 606/232 |
| 5,350,380 A | 9/1994 | Goble et al. | 606/80 |
| 5,352,229 A | 10/1994 | Goble et al. | 606/72 |
| 5,354,299 A | 10/1994 | Coleman | 606/73 |
| 5,356,413 A | 10/1994 | Martins et al. | 606/75 |
| 5,358,511 A | 10/1994 | Gatturna et al. | 606/232 |
| 5,364,400 A | 11/1994 | Rego, Jr. et al. | 606/72 |
| 5,372,599 A | 12/1994 | Martins | 606/75 |
| 5,376,119 A | 12/1994 | Zimmerman et al. | 673/13 |
| RE34,841 E | 1/1995 | Suovaniemi et al. | 606/73 |
| 5,383,878 A | 1/1995 | Roger et al. | 606/73 |
| 5,391,170 A | 2/1995 | McGuire et al. | 606/86 |
| 5,393,302 A | 2/1995 | Clark et al. | 623/13 |
| 5,397,356 A | 3/1995 | Goble et al. | 623/13 |
| 5,411,506 A | 5/1995 | Goble et al. | 606/104 |
| 5,411,523 A | 5/1995 | Goble | 606/232 |
| 5,417,712 A | 5/1995 | Whittaker et al. | 606/232 |
| 5,423,819 A | 6/1995 | Small et al. | 606/73 |
| 5,425,733 A | 6/1995 | Schmieding | 606/104 |
| 5,425,767 A | 6/1995 | Steininger et al. | 623/13 |
| 5,431,651 A | 7/1995 | Goble | 606/73 |
| 5,443,509 A | 8/1995 | Boucher et al. | 623/16 |
| 5,454,811 A | 10/1995 | Huebner | 606/60 |
| 5,456,685 A | 10/1995 | Huebner | 606/73 |
| 5,458,601 A | 10/1995 | Young, Jr. et al. | 606/72 |
| 5,464,427 A | 11/1995 | Curtis et al. | 606/232 |
| 5,470,334 A | 11/1995 | Ross et al. | 606/72 |
| D368,777 S | 4/1996 | Goble et al. | D24/145 |
| 5,505,735 A | 4/1996 | Li | 606/72 |
| 5,527,342 A | 6/1996 | Pietrzak et al. | 606/232 |
| 5,545,180 A | 8/1996 | Le et al. | 606/232 |
| D374,286 S | 10/1996 | Goble et al. | D24/145 |
| D374,287 S | 10/1996 | Goble et al. | D24/145 |
| D374,482 S | 10/1996 | Goble et al. | D24/145 |
| 5,562,671 A | 10/1996 | Goble et al. | 606/73 |
| D375,791 S | 11/1996 | Goble et al. | D24/145 |
| 5,571,104 A | 11/1996 | Li | 606/72 |
| 5,571,184 A | 11/1996 | DeSatnick | 623/13 |
| 5,573,548 A | 11/1996 | Nazre et al. | 606/232 |
| 5,584,835 A | 12/1996 | Greenfield | 606/73 |
| 5,601,562 A * | 2/1997 | Wolf et al. | 606/86 |
| 5,632,748 A | 5/1997 | Beck, Jr. et al. | 606/89 |
| 5,643,266 A | 7/1997 | Li | 606/72 |
| 5,643,321 A | 7/1997 | McDevitt | 606/232 |
| 5,645,547 A | 7/1997 | Coleman | 606/73 |
| 5,645,589 A | 7/1997 | Li | 623/16 |
| 5,647,874 A | 7/1997 | Hayhurst | 606/72 |
| 5,649,963 A | 7/1997 | McDevitt | 606/232 |
| 5,662,654 A | 9/1997 | Thompson | 606/72 |
| 5,702,397 A | 12/1997 | Goble et al. | 606/72 |
| 5,707,395 A | 1/1998 | Li | 606/232 |
| 5,713,897 A | 2/1998 | Goble et al. | 606/53 |
| 5,718,706 A | 2/1998 | Roger | 606/73 |
| 5,720,753 A | 2/1998 | Sander et al. | 606/104 |
| 5,766,250 A | 6/1998 | Chervitz et al. | 623/13 |
| 5,769,894 A | 6/1998 | Ferragamo | 623/13 |
| 5,899,938 A | 5/1999 | Sklar et al. | 623/13 |
| 5,951,560 A | 9/1999 | Simon et al. | 606/73 |
| 6,235,057 B1 * | 5/2001 | Roger et al. | 623/13.12 |
| 6,355,066 B1 * | 3/2002 | Kim | 606/232 |

* cited by examiner

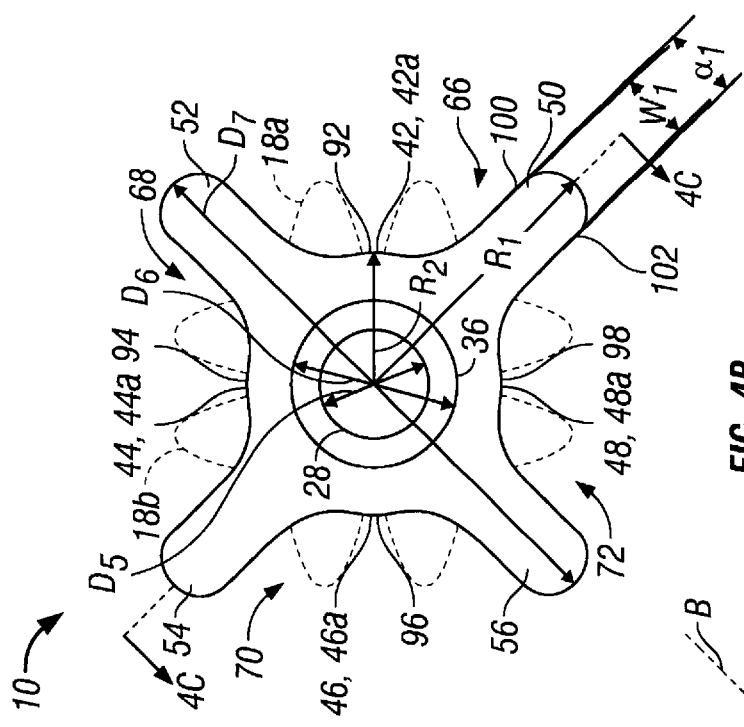
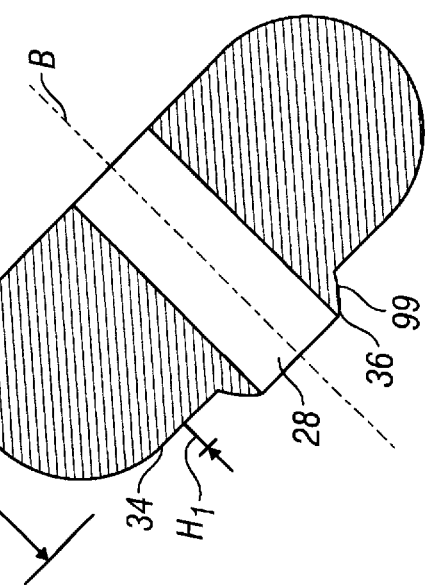
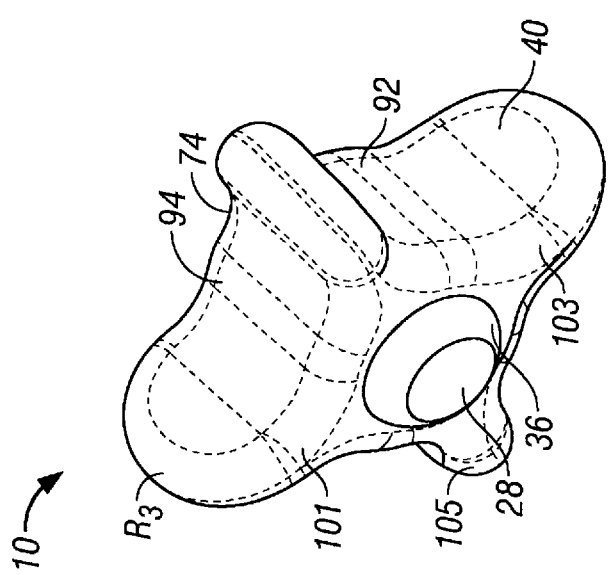
FIG. 4B
FIG. 4C
FIG. 4A

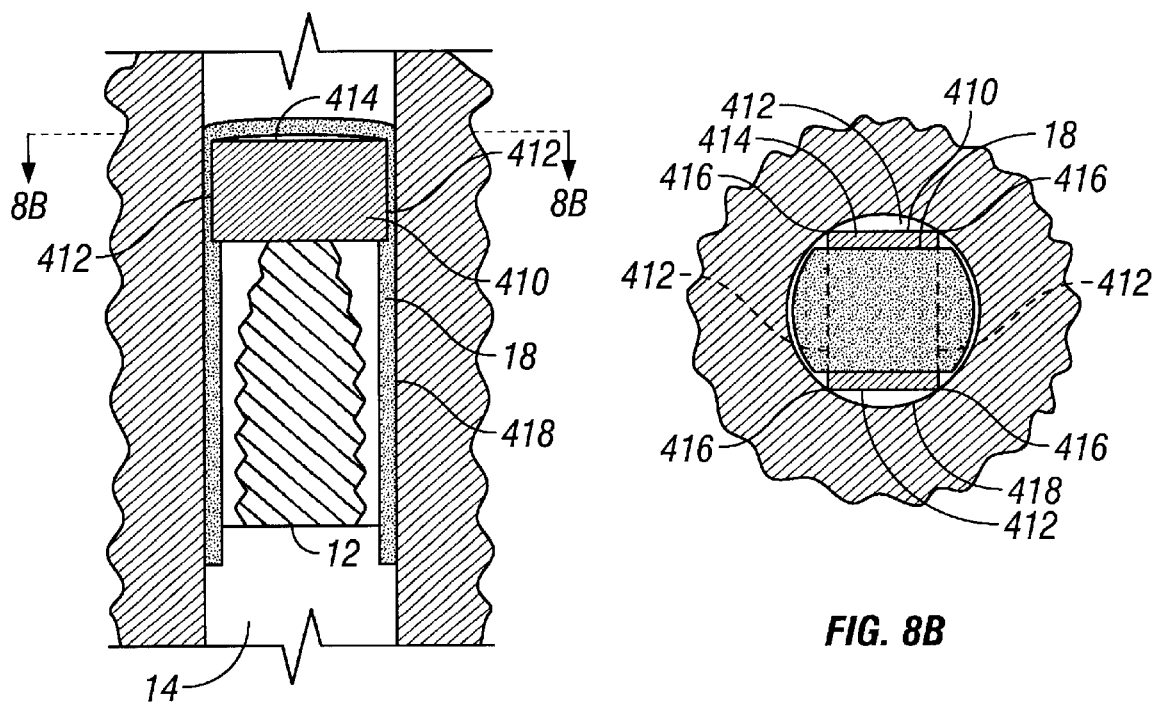
FIG. 8A
FIG. 8B
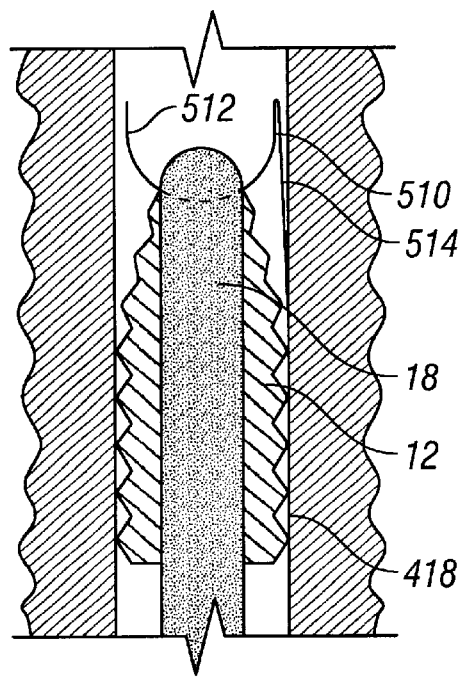
FIG. 9

GRAFT ANCHOR

BACKGROUND

This invention relates to a graft anchor for securing a graft in a bone tunnel.

A torn ligament is a common injury. One way to treat the injury is to replace the ligament with a soft tissue or synthetic graft, formed from a ligament or tendon tissue or synthetic material. A surgeon drills a tunnel in the bone, and positions one end of the graft in the tunnel. An interference screw is positioned in the tunnel adjacent the graft to urge the graft against the wall of the tunnel.

SUMMARY

According to one aspect of the invention, a device for securing a graft in a bone tunnel includes an anchoring member having a graft supporting surface. The anchoring member is configured to be positioned within the bone tunnel distal of an interference member with the graft retained by the graft supporting surface and extending proximally from the anchoring member. The anchoring member has an engaging surface for engaging a distal end of the interference member to limit movement of the graft relative to the interference member.

Embodiments of this aspect of the invention may include one or more of the following features.

The engaging surface is an end face of the anchoring member. The end face has a coupling member configured to interface with the interference member. The coupling member is a protruding nib sized to fit within an opening in an end of the interference member. The nib is located in a center portion of the anchoring member. Alternatively, the nib is located off-center of the anchoring member.

The graft supporting surface is constructed to receive a graft looped around the anchoring member, and is formed by an exterior surface of the anchoring member. The anchoring member is a generally planar structure including four sides, a top face, and a bottom face forming the engaging surface. The graft supporting surface includes at least one of the four sides and the top face. The top face is indented. The four sides are flat.

The graft supporting surface includes a first indented surface defined by a first side of the anchoring member, a second indented surface defined by a second opposing side of the anchoring member, a third indented surface defined by a third side of the anchoring member, and a fourth indented surface defined by a fourth side of the anchoring member. Alternatively, the third and fourth sides of the anchoring member are not part of the graft supporting surface, and are convex surfaces.

The anchoring member defines a bore for receiving a guide wire. The bore is located in the center of the anchoring member. Alternatively, the bore is located off-center. The nib is located circumferentially about the bore.

In another aspect, an anchoring member for securing a graft in a bone tunnel includes a generally planar structure having a first side, an opposing second side, a distal end, and a proximal end face. The first side defining a first indentation for receiving the graft and the second side defines a second indentation for receiving the graft. The end face includes a protruding nib configured to fit within an opening in an end of an interference member. The structure defines a bore for receiving a guide wire. The anchoring member is configured to be positioned within the bone tunnel distal of an interference member with the protruding nib interfacing with the interference member and with the graft looped around the distal end of the structure and retained in the first and second indentations. The anchoring member limits movement of the graft relative to the interference member.

According to another aspect, the invention features a method for securing a graft in a bone tunnel. The method includes providing an anchoring member having a graft supporting surface; looping the graft over the anchoring member so that the graft is retained by the graft supporting surface; inserting the anchoring member and graft into the bone tunnel; and inserting an interference member into the bone tunnel adjacent the graft and proximal of the anchoring member so that the anchoring member engages a distal end of the interference member to limit movement of the graft relative to the interference member.

Embodiments of this aspect of the invention may include one or more of the following features.

The anchoring member is loaded onto a guide wire. Inserting the anchoring member includes inserting the anchoring member and graft into the bone tunnel with the guide wire. The anchoring member is loaded onto a distal end of the guide wire such that the anchoring member abuts a ledge defined by the guide wire. The ledge limits proximal movement of the anchoring member relative to the guide wire.

Inserting the interference member, e.g., an interference screw, into the bone tunnel includes distally advancing the interference member over a guide wire, and abutting the distal end of the interference member against an end face of the anchoring member. The end face includes a protruding nib and an end of the interference member is placed over the nib.

According to another aspect of the invention, a device for securing a graft in a bone tunnel includes an anchoring member, an interference member, and a guide wire. The anchoring member has a graft supporting surface. The anchoring member is configured to be positioned within the bone tunnel with the graft retained by the graft supporting surface and extending proximally from the anchoring member. The anchoring member defines a first bore of a first diameter. The interference member defines a second bore of a second diameter larger than the first diameter. The guide wire has a first region and a second region of a different diameter than the first region. The first and second regions of the guide wire define a shelf therebetween. The diameter of the second region of the guide wire is larger than the diameter of the first bore. The first region is insertable into the first bore with the shelf abutting the anchoring member and the interference member is insertable over the guide wire to abut the anchoring member.

Embodiments of this aspect of the invention may include a guide wire having locating mark for indicating the position of the interference member within the bone tunnel.

According to another aspect of the invention, a device for securing a graft in a bone tunnel includes an anchoring member and a guide wire. The anchoring member has a graft supporting surface. The anchoring member is configured to be positioned within the bone tunnel with the graft retained by the graft supporting surface and extending proximally from the anchoring member. The anchoring member defines a bore. The guide wire includes a first region and a second region of a different diameter than the first region. The first and second regions of the guide wire define a shelf therebetween. The diameter of the second region is larger than a diameter of the bore. The first region is insertable into the bore with the shelf abutting the anchoring member.

Among other advantages, the invention is easy to use and provides a reliable way of avoiding the graft from slipping between the interference screw and the side of the bone hole. As a result, the invention helps assure that the graft will remain securely in place even when tension is applied to it. Because the graft is directly retained by the graft supporting surface of the anchoring member, there is no need to take more elaborate measures (such as attempting to retain the graft with suture) to help prevent the graft from slipping. Furthermore, the surgeon can properly position the interference member in the bone relative to the anchoring member by simply using markings on the guide wire.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 4A–4C are perspective, top, and cross-sectional side views, respectively, of the anchoring member of FIG. 1;

FIGS. 8A and 8B are side and end views of an additional alternative embodiment of an anchoring member shown securing a graft in a bone tunnel; and FIG. 9 is a side view of an additional alternative embodiment of an anchoring member shown securing a graft in a bone tunnel.

DETAILED DESCRIPTION

Figure 1:
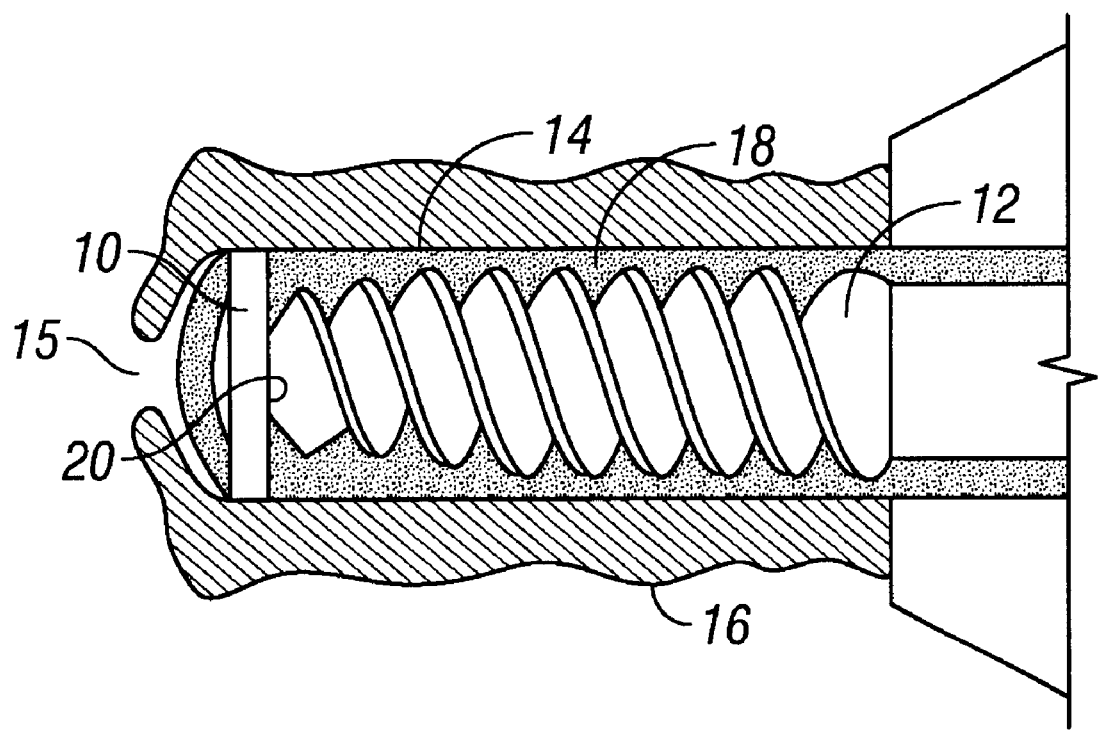
FIG. 1 is a side view of an anchoring member and interference screw, shown securing a graft in a bone tunnel.

Referring to FIG. 1, an anchoring member 10 and an interference member, e.g., an interference screw 12, act together to secure a graft 18, e.g., a soft tissue or synthetic graft, formed from a ligament or tendon tissue or synthetic material, within a bone tunnel 14 formed in a femur 16. Graft 18 is looped around anchoring member 10 and extends proximately from anchoring member 10 and out of tunnel 14. Anchoring member 10 is positioned distal of screw 12 with anchoring member 10 abutting a distal end 20 of screw 12. Sliding of graft 18 relative to screw 12 when the graft is under tension is limited by the placement of anchoring member 10 distal to screw 12. Screw 12 restrains anchoring member 10 from moving proximally. Because graft 18 is looped around anchoring member 10, graft 18 is also restrained from slipping proximally and thus loosening. The desired tension is thereby maintained in graft 18.

Figure 2:
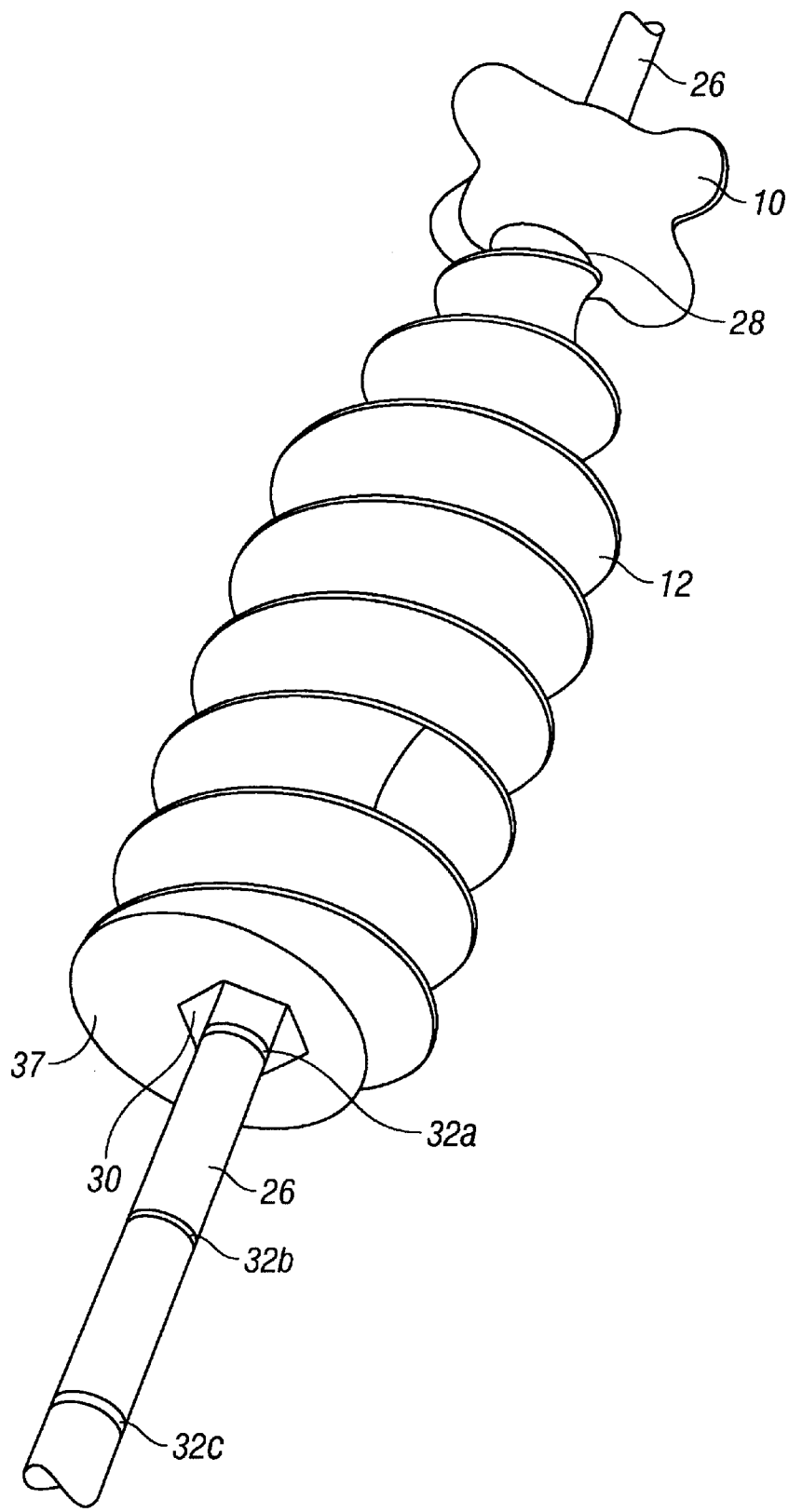
FIG. 2 is a perspective view of the anchoring member and interference screw of FIG. 1, shown mounted on a guide wire.
Figure 3:
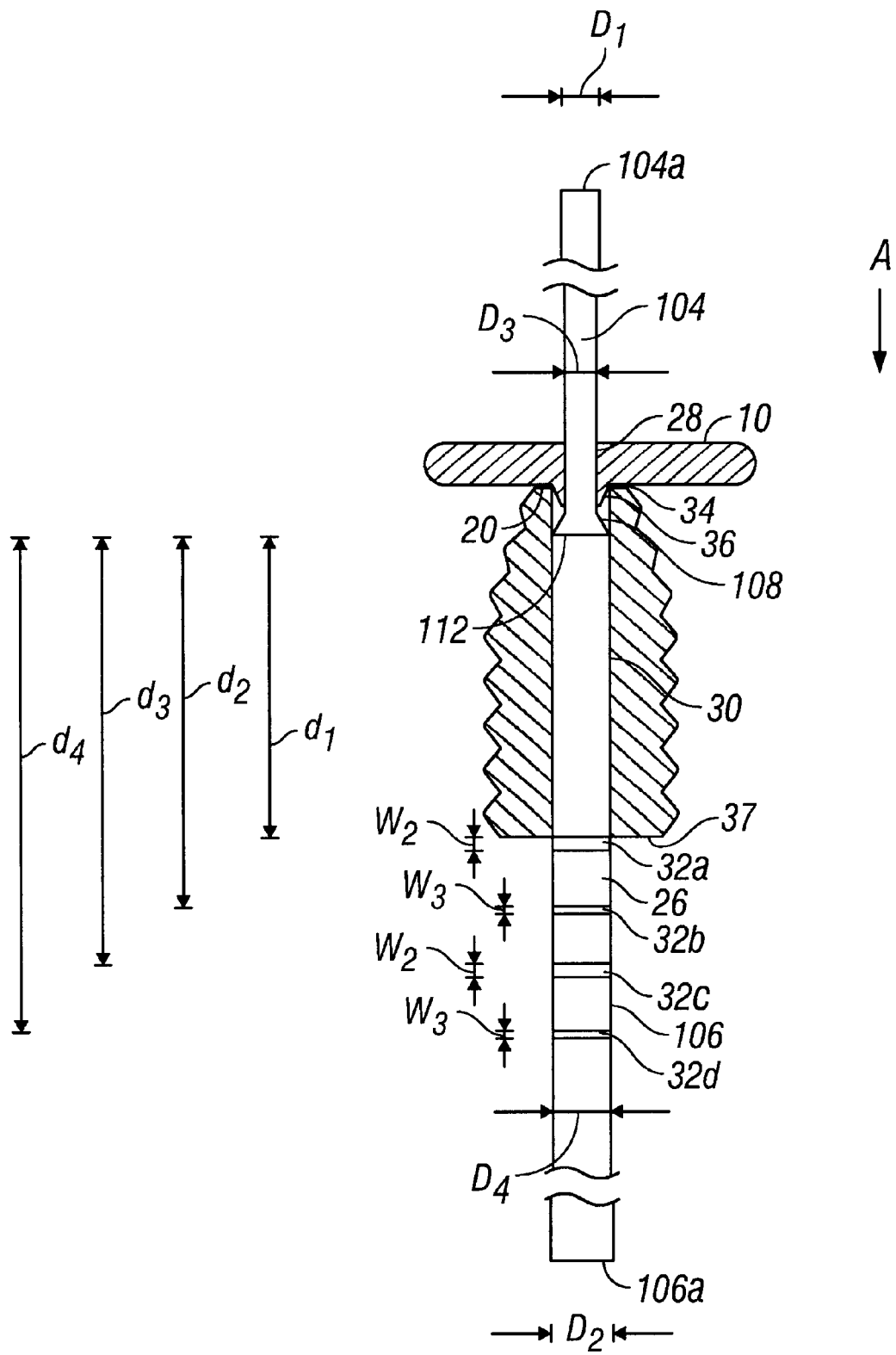
FIG. 3 is a cross-sectional side view of the anchoring member, interference screw, and guide wire of FIG. 2.

Referring to FIGS. 2 and 3, anchoring member 10 and screw 12 define longitudinal through bores 28, 30, respectively, for receiving a guide wire 26. The diameter, $D_1$, of anchoring member bore 28 is smaller than the diameter, $D_2$, of screw bore 30. Guide wire 26 has a distal section 104 received within anchoring member bore 28, and a proximal section 106 received within screw bore 30. Guide wire 26 has a distal end 104a and a proximal end 106a. The diameter, $D_3$, of distal section 104 is smaller than the diameter, $D_4$, of proximal section 106 forming a tapered ledge 108 between the sections. In use, anchoring member 10 is slid onto distal section 104 of guide wire 26 in the direction of arrow, A, until proximal advancement of anchoring member 10 is stopped by the abutment of anchoring member 10 with ledge 108.

Anchoring member 10 has an end face 34 which, in use, engages distal end 20 of interference screw 12. End face 34 includes a central, protruding nib 36 which is received within screw bore 30 to maintain anchoring member 10 centered on screw 12 after removal of guide wire 26. Nib 36 is circumferentially disposed about bore 28.

Screw 12 is a standard interference screw, e.g. Smith and Nephew screw 7207180.

Guide wire 26 has locating marks 32a, 32b, 32c, 32d disposed at regular intervals along a length of second section 106. Marks 32a–32d can be formed, e.g., by laser marking. Marks 32a–32d are used to determine when screw 12 has been advanced into engagement with anchoring member 10 to assist the surgeon in correctly placing screw 12 in tunnel 18. When screw 12 is first placed on guide wire 26, it may cover one or more of locating marks 32a–32d. As the surgeon moves screw 12 distally along guide wire 26, depending upon the length of screw 12, the surgeon aligns proximal end 37 of screw 12 with the correct mark which indicates that distal end 20 of screw 12 is in contact with anchoring member 10.

Referring to FIGS. 4A–4C, anchoring member 10 is in the form of a generally planar structure 40 having four sides 42, 44, 46, 48, end face 34, and top face 74. Each side 42, 44, 46, 48 has a generally concave shape forming a graft supporting surface portions 42a, 44a, 46a and 48a, respectively, and arms 50, 52, 54 and 56. Surfaces 42a, 44a, 46a, and 48a each define an indentation 66, 68, 70 and 72, respectively. A bump 92, 94, 96 and 98 extends into each indentation 66, 68, 70 and 72, respectively. Graft 18 is received within indentations 66, 68, 70 and 72, with one graft strand 18a extending distally through indentation 66, over top face 74, and proximally through indentation 70; and a second graft strand 18b extending distally through indentation 68, over top face 74, and proximally through indentation 72. Bumps 92, 94, 96 and 98 help to guide the graft strands around guide wire 26 when the graft strands are placed over top face 74 to limit interference of the graft strands with distal section 104 of guide wire 26 (located in bore 28). Thus, graft 18 is supported by graft supporting surface, comprising portions 42a, 44a, 46a, and 48a and top face 74. Arms 50, 52, 54 and 56 help to assure that the graft strands do not slip off anchoring member 10.

Anchoring member 10 is dimensioned such that the diameter of end face 34 is large enough to prevent anchoring member 10 from being able to slide proximal of distal end 20 of screw 12, and such that arms 50, 52, 54 and 56 engage a side of bone tunnel 14 so that graft 18 does not slip out of indentations 66, 68, 70 and 72. Anchoring member 10 is not so thick that it takes up too much space in tunnel 18, but it is thick enough to support graft 18. Nib 36 is configured to fit into screw bore 30, so that anchoring member engages screw 12.

More specifically, nib 36 and bore 28 are centrally located about axis, B. Nib 36 has a sloped sidewall 99 with a lower diameter $D_5$ of, e.g., about 0.060" (1.52 mm) and an upper diameter $D_6$ of, e.g., about 0.090" (2.29 mm). Nib 36 has a height $H_1$ of, e.g., about 0.019" (0.483 mm). Anchoring member 10 has a height $H_2$, excluding nib 36, of about 0.125" (3.18 mm). Bore 28 diameter $D_1$ is, e.g., about 0.060" (1.52 mm).

Arms 50, 52, 54, 56 each have a radius $R_1$, measured from a center of bore 28, of, e.g., about 0.158" (4.01 mm). Thus, anchoring member 10 has a diameter $D_7$ of, e.g., about 0.316" (8.02 mm). Bumps 92, 94, 96, 98 between arms 50, 52, 54, 56 each have a radius $R_2$, measured from a center of bore 28, of, e.g., about 0.072" (1.83 mm). Arms 50, 52, 54, 56 have a width $W_1$ of, e.g., about 0.041" (1.04 mm). Sides 100, 102 of arm 50 form an angle $\alpha_1$ of, e.g., about 2.35°. Anchoring member 10 can be formed from a metal, preferably titanium, or a polymer, preferably a bioabsorbable maternal such as polylactic acid (PLA). Edges 101, 103, 105 of anchoring member 10 have a radius $R_3$ of, e.g., about 0.020" (0.508 mm).

Guide wire diameter $D_3$ is, e.g., about 0.059" (1.50 mm), and guide wire diameter $D_4$ is e.g. about 0.079" (2.01 mm), forming ledge 108 with a sufficient width to prevent anchoring member 10 from moving proximally of ledge 108 when graft 18 is under tension. Marks 32a, 32b, 32c and 32d are arranged to correspond to different length screws 12. Marks 32a, 32c have widths different from widths of marks 32b, 32b. These widths allow a surgeon to quickly discern which marks are exposed by interference screw 12. Mark 32a is at a distance $d_1$ of, e.g., about 0.776" (19.7 mm) from ledge end 112, mark 32b is a distance $d_2$ of, e.g., about 0.978" (24.8 mm) from end 112, mark 32c is a distance $d_3$ of, e.g., about 1.170" (29.7 mm) from end 112, and mark 32d is a distance $d_4$ of, e.g., about 1.372" (34.8 mm) from end 112. Marks 32a, 32c have a width $W_2$ of, e.g., about 0.02" (0.508 mm). Marks 32b, 32d have a width $W_3$ of, e.g., about 0.01" (0.254 mm).

In use, the surgeon loads the anchoring member 10 onto distal section 104 of guide wire 26 and proximally advances anchoring member 10 until anchoring member 10 abuts guide wire ledge 108. Ledge 108 prevents further proximal movement of anchoring member 10 along guide wire 26. The surgeon then loops the graft strands over graft supporting surface, including portions 42a, 44a, 46a, and 48a and top face 74, of anchoring member 10 with the graft strands retained in indentations 66, 68, 70 and 72. The surgeon positions anchoring member 10 and graft 18 in bone tunnel 14 by inserting the guide wire 26 into the tunnel. Guide wire 26 can be pushed or pulled through tunnel 14. Guide wire extends through a distal guide wire bore 15 (FIG. 1) in femur 16, extending from tunnel 14 to a surface of the femur. The surgeon then loads screw 12 onto proximal section 106 of guide wire 26 and distally advances the screw into the bone tunnel over the guide wire. For the length of screw 12 shown in FIG. 3, screw 12 is advanced until proximal end 37 of screw 12 is aligned with mark 32a. This signals the surgeon that screw 12 has been fully advanced into engagement with anchoring member 10.

With screw 12 fully advanced into tunnel 18, screw 12 is proximal of anchoring member 10 with end face 34 of anchoring member 10 engaging distal end 20 of screw 12. Screw 12 is located in the middle of the graft strands, thereby urging the graft strands against the bone tunnel wall. Tension applied to the graft will not cause the graft to slip proximally relative to screw 12 because graft 18 is retained by anchoring member 10. The graft is supported by graft supporting surface 42a, 44a, 46a and 48a and top face 74 of anchoring member 10.

Other embodiments are within the scope of the following claims.

Figure 5A:
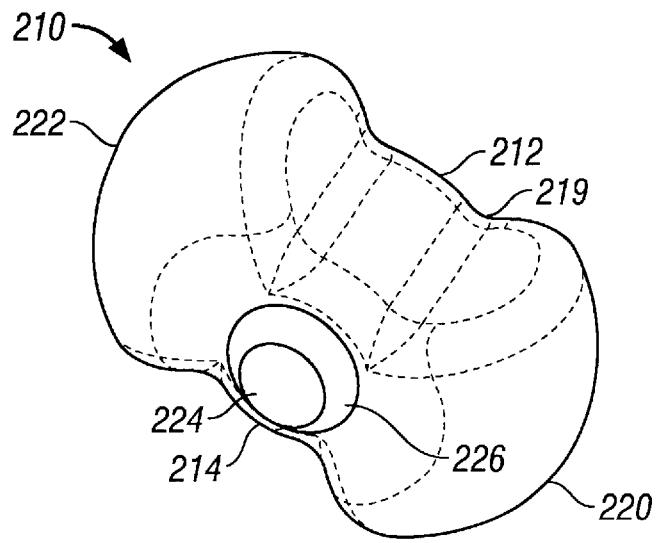
FIGS. 5A–5C are perspective, top, and cross-sectional side views, respectively, of an alternative embodiment of an anchoring member.
Figure 5B:
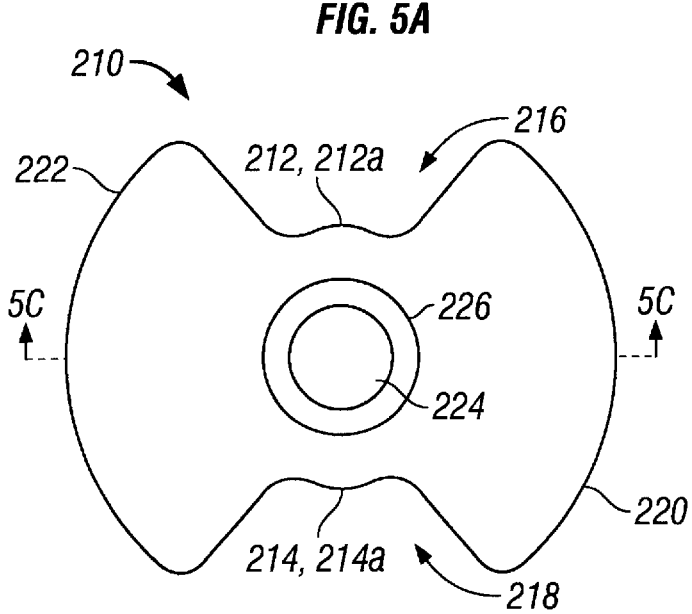
Figure 5C:
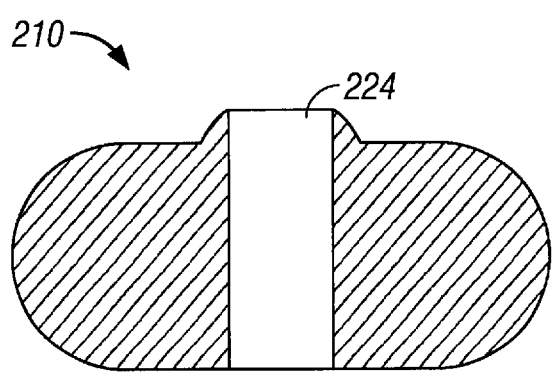

For example, referring to FIGS. 5A–5C an anchoring member 210 has only two graft supporting surfaces on the sides of anchoring member 210. This configuration results in the graft being positioned on only two sides of screw 12, thereby leaving two sides of screw 12 free to engage sidewalls of tunnel 14. Anchoring member 210 has first and second opposing sides 212, 214 including graft supporting surfaces 212a, 214a, and third and fourth opposing sides 220, 222. Graft supporting surfaces 212a, 214a define indentations 216, 218, respectively, for receiving the graft. The graft is looped around anchoring member 210 and supported by graft supporting surfaces 212a and 214a and a top face 219. Sides 220, 222 have a generally convex shape, for abutting sidewalls of a bone tunnel. Anchoring member 210 defines a central bore 224 configured for receiving a guide wire and includes a protruding nib 226.

Figure 6A:
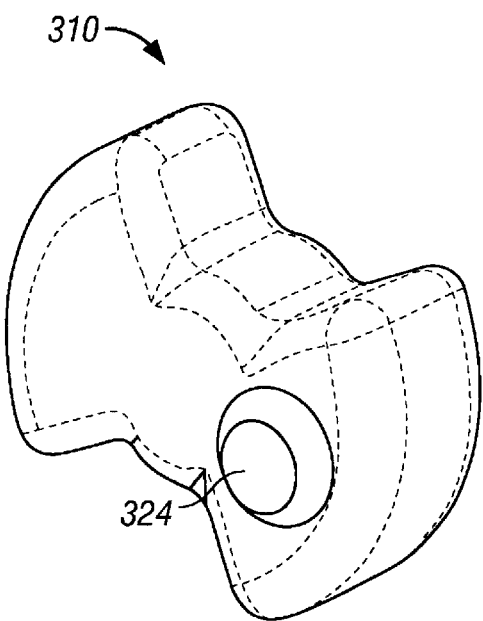
FIGS. 6A–6C are perspective, top, and side views of an additional alternative embodiment of an anchoring member.
Figure 6B:
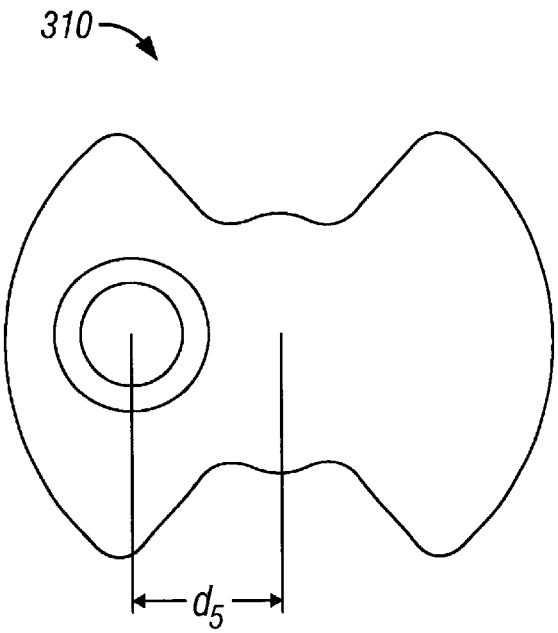
Figure 6C:
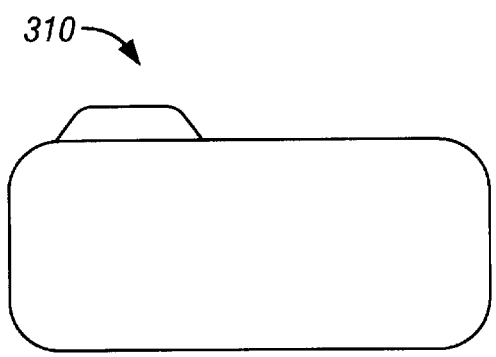
Figure 7:
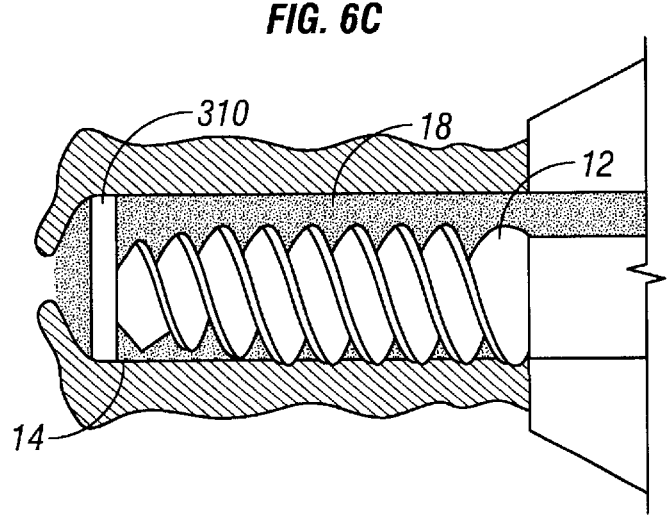
FIG. 7 is a side view of the anchoring member of FIGS. 6A–6C and an interference screw, shown securing a graft in a bone tunnel.

Referring to FIGS. 6A–6C, in another alternative embodiment, an anchoring member 310 defines a bore 324 located off-center of anchoring member 310. Thus, graft 18 can be looped over anchoring member 310 and positioned to one side of interference screw 12, leaving screw 12 free to engage the tunnel wall, as shown in FIG. 7.

Bore 324 is located a distance $d_5$ of, e.g., about 0.080" (2.03 mm) from the center of anchoring member 310. Likewise, in the embodiment of FIGS. 4A–4C, bore 28 can be located off-center of anchoring member 10.

The graft supporting surfaces defined by the sidewalls of the anchoring member, rather than being external surfaces, can be formed internally in the anchoring member. For example, two additional bores can be defined by the anchoring member through which the graft can be passed to loop the graft around the anchoring member.

Referring to FIGS. 8a and 8b, an anchoring member 410 is cube shaped with sidewalls 412 and top surface 414 acting as graft supporting surfaces. Edges 416 of the cube contact wall 418 of bone tunnel 14 such that graft 18 is retained within the space defined between anchoring member 410 and bone tunnel wall 418. Anchoring member 410 can be a bone block harvested from the patient (or another source) and formed into a suitable shape by the surgeon. Graft 18 is looped over the bone block.

The top surface of the anchoring member can also be indented. As shown in FIG. 9, the anchoring member 510 can be a wire form having a U-shaped portion 512 distal of screw 12 and a portion 514 extending proximally between screw 12 and bone wall 418 to limit rocking of anchoring member 510. Graft 18 is retained within portion 512 to prevent slipping of graft 18 relative to screw 12. The base of the U-shape engages the distal tip of screw 12.

A number of embodiments of the invention have been described. Nevertheless, it will be understood that various modifications may be made without departing from the spirit and scope of the invention. Accordingly, other embodiments are within the scope of the following claims.

What is claimed is:

1. A device for securing a graft in a bone tunnel, comprising:
   an interference member configured to be positioned within the bone tunnel; and
   an anchoring member including a graft supporting surface, the anchoring member being configured to be positioned within the bone tunnel distal of the interference member with the graft retained by the graft supporting surface and extending proximally from the anchoring member, the anchoring member having an engaging surface for engaging a distal end of the interference member to limit movement of the graft relative to the interference member.

2. The device of claim 1 wherein the engaging surface comprises an end face of the anchoring member.

3. A device for securing a graft in a bone tunnel, comprising:

an anchoring member including a graft supporting surface, the anchoring member being configured to be positioned within the bone tunnel distal of an interference member with the graft retained by the graft supporting surface and extending proximally from the anchoring member, the anchoring member having an engaging surface for engaging a distal end of the interference member to limit movement of the graft relative to the interference member, wherein the engaging surface comprises an end face of the anchoring member, and wherein the end face includes a coupling member configured to interface with the interference member.

4. The device of claim 3 wherein the coupling member comprises a protruding nib sized to fit within an opening in an end of the interference member.

5. The device of claim 4 wherein the nib is located in a center portion of the anchoring member.

6. The device of claim 5 wherein the nib is located off-center of the anchoring member.

7. The device of claim 1 wherein the graft supporting surface is constructed to receive a graft looped around the anchoring member.

8. The device of claim 1 wherein the graft supporting surface comprises an exterior surface of the anchoring member.

9. A device for securing a graft in a bone tunnel, comprising:

an anchoring member including a graft supporting surface, the anchoring member being configured to be positioned within the bone tunnel distal of an interference member with the graft retained by the graft supporting surface and extending proximally from the anchoring member, the anchoring member having an engaging surface for engaging a distal end of the interference member to limit movement of the graft relative to the interference member, wherein the anchoring member is a generally planar structure including four sides.

10. The device of claim 9 wherein the generally planar structure further includes a top face and a bottom face, the bottom face comprising the engaging surface.

11. The device of claim 10 wherein the graft supporting surface comprises at least one of the four sides and the top face.

12. The device of claim 10 wherein the top face is indented.

13. The device of claim 9 wherein the graft supporting surface comprises a first indented surface defined by a first side of the anchoring member and a second indented surface defined by a second opposing side of the anchoring member.

14. The device of claim 13 wherein the graft supporting surface further comprises a third indented surface defined by a third side of the anchoring member and a fourth indented surface defined by a fourth side of the anchoring member.

15. The device of claim 13 wherein third and fourth sides of the anchoring member comprise convex surfaces.

16. The device of claim 9 wherein the four sides are flat.

17. A device for securing a graft in a bone tunnel, comprising:

an anchoring member including a graft supporting surface, the anchoring member being configured to be positioned within the bone tunnel distal of an interference member with the graft retained by the graft supporting surface and extending proximally from the anchoring member, the anchoring member having an engaging surface for engaging a distal end of the interference member to limit movement of the graft relative to the interference member, wherein the anchoring member defines a bore for receiving a guide wire.

18. The device of claim 17 wherein the bore is located in a center portion of the anchoring member.

19. The device of claim 17 wherein the bore is located off-center of the anchoring member.

20. The device of claim 17 wherein the anchoring member includes an end face with a protruding nib, the nib being located circumferentially about the bore.

21. An anchoring member for securing a graft in a bone tunnel, comprising:

a generally planar structure including a first side, an opposing second side, a distal end, and a proximal end face, the first side defining a first indentation for receiving the graft and the second side defining a second indentation for receiving the graft, the end face including a, protruding nib configured to fit within an opening in an end of an interference member, the structure defining a bore for receiving a guide wire, the anchoring member being configured to be positioned within the bone tunnel distal of an interference member with the protruding nib interfacing with the interference member and with the graft looped around the distal end of the structure and retained in the first and second indentations, the anchoring member limiting movement of the graft relative to the interference member.

22. A method for securing a graft in a bone tunnel, comprising:

providing an anchoring member including a graft supporting surface, looping the graft over the anchoring member such that the graft is retained by the graft supporting surface, inserting the anchoring member and graft into the bone tunnel, and inserting an interference member into the bone tunnel adjacent the graft and proximal of the anchoring member so that the anchoring member engaging a distal end of the interference member to limit movement of the graft relative to the interference member.

23. The method of claim 22 further comprising:

loading the anchoring member onto a guide wire, wherein the step of inserting the anchoring member includes inserting the anchoring member and graft into the bone tunnel with the guide wire.

24. The method of claim 23 wherein the step of loading the anchoring member onto a guide wire includes loading the anchoring member onto a distal end of the guide wire such that the anchoring member abuts a ledge defined by the guide wire, the ledge limiting proximal movement of the anchoring member relative to the guide wire.

25. The method of claim 22 wherein the step of inserting an interference member into the bone tunnel includes distally advancing the interference member over a guide wire.

26. The method of claim 22 wherein the step of inserting an interference member into the bone tunnel comprises inserting an interference screw.

27. The method of claim 22 wherein the step of inserting an interference member includes abutting the distal end of the interference member against an end face of the anchoring member.

28. The method of claim 27 wherein the end face includes a protruding nib and the step of inserting an interference member includes placing an end of the interference member over the nib.

29. A device for securing a graft in a bone tunnel, comprising:

an anchoring member including a graft supporting surface, the anchoring member being configured to be positioned within the bone tunnel with the graft retained by the graft supporting surface and extending proximally from the anchoring member, the anchoring member defining a first bore of a first diameter, an interference member defining a second bore of a second diameter larger than the first diameter, and a guide wire including a first region and a second region of a different diameter than the first region, the first and second regions of the guide wire defining a shelf therebetween, the diameter of the second region being larger than the diameter of the first bore, the first region being insertable into the first bore with the shelf abutting the anchoring member, and the interference member being insertable over the guide wire to abut the anchoring member.

30. The device of claim 29 wherein the guide wire includes a locating mark for indicating the position of the interference member within the bone tunnel.

31. A device for securing a graft in a bone tunnel, comprising:

an anchoring member including a graft supporting surface, the anchoring member being configured to be positioned within the bone tunnel with the graft retained by the graft supporting surface and extending proximally from the anchoring member, the anchoring member defining a bore, and a guide wire including a first region and a second region of a different diameter than the first region, the first and second regions of the guide wire defining a shelf therebetween, the diameter of the second region being larger than a diameter of the bore, the first region being insertable into the bore with the shelf abutting the anchoring member.

* * * * *